(12) United States Patent
McKee et al.

(10) Patent No.: US 8,754,641 B1
(45) Date of Patent: Jun. 17, 2014

(54) HORSE HOOF ANGLE MEASURING DEVICE

(76) Inventors: Samuel S. McKee, Ocala, FL (US); Roy A. Young, Odessa (CA)

(*) Notice: Subject to any disclaimer, the term of this patent is extended or adjusted under 35 U.S.C. 154(b) by 150 days.

(21) Appl. No.: 13/609,554

(22) Filed: Sep. 11, 2012

(51) Int. Cl.
*G01R 33/07* (2006.01)
*A01L 11/00* (2006.01)

(52) U.S. Cl.
USPC .............................. 324/251; 33/195; 168/45

(58) Field of Classification Search
USPC .............................. 324/251; 33/195; 168/45
See application file for complete search history.

(56) References Cited

U.S. PATENT DOCUMENTS

| 832,060 | A | 10/1906 | Holmquist |
| 3,494,044 | A | 2/1970 | Sayers |
| 4,214,370 | A | 7/1980 | Beaston |
| 4,227,311 | A | 10/1980 | Behney |
| 4,813,148 | A | 3/1989 | Finnegan |
| 5,027,520 | A | 7/1991 | Finnegan |

*Primary Examiner* — Bot Ledynh
(74) *Attorney, Agent, or Firm* — Sven W Hanson

(57) ABSTRACT

The invention provides a hoof angle measuring device for use on horses. A base is configured to be held against the bottom of a horse hoof and a pivoting arm can then be aligned with the forward edge of the hoof to define the hoof angle. Without physical or electrical contact with the base or arm, an enclosed sensor detects relative angular position between the base and arm. Supporting circuitry also provided in an enclosure accepts signal voltage from the sensor and provides a protected digital display of the measured angle magnitude for the user.

4 Claims, 6 Drawing Sheets

HORSE HOOF ANGLE MEASURING DEVICE

BACKGROUND OF THE INVENTION

The present invention pertains to devices for measuring physical parameters of a horse's hoof in the context of caring for horses. Particularly, the invention presents devices and methods for measuring the angle between the forward surface of the hoof and the plane of the bottom of the hoof. Measuring of this angle is essential to the task of caring for the legs and feet of a horse and in shoeing a horse.

These aspects are well known and various devices have been developed to measure different physical parameters of horse hoofs. Despite the long history of this art and science, the tools available for this work continue to be very crude. This is believed to be, at least in part, due to the rough and extreme environment presented by horses and their care. Care of horses is often in uncontrolled environment and present many sources of dirt, water, and other sources of abrasive or corrosive materials that may harm delicate or precise tools. In addition, movement of horses and their surrounding equipment pose risk of impact damage. For these reasons, prior art farrier tools including hoof angle measuring tools are often large and durable and consequently lacking in precision. What is needed is an easily used, yet precise angle measuring device with a design that can survive the inherent environment of equine care.

SUMMARY OF THE INVENTION

The present invention presents a device that measures relative angular position between hoof angle-defining components using electronic measuring device while maintaining the measuring device physically and electrically isolated from the angle-defining components that contact the horse hoof during use.

The invention provides a base element configured to be held against the bottom of a horse hoof and a pivoting arm that can then be aligned with the forward edge of the hoof to define the hoof angle. An electronic sensor is contained isolated in an enclosure. Without physical or electrical contact with the base or arm, the sensor detects relative angular position between the base and arm. Supporting circuitry also provided in an enclosure accepts a signal voltage from the sensor and provides for the user a protected digital display of the measured angle magnitude.

Preferably, the sensor includes a Hall Effect device selected or configured to respond to angular orientation of a nearby magnetic field. A magnet is secured to the arm to enable the sensor to detect orientation of the arm. Other configurations are contemplated wherein the sensor uses other means for measuring relative angle without contact.

Additional novel aspects and benefits of the invention will be discerned from the following description of particular embodiments and the accompanying figures.

DETAILED DESCRIPTION OF EMBODIMENTS OF THE INVENTION

Figure 1:
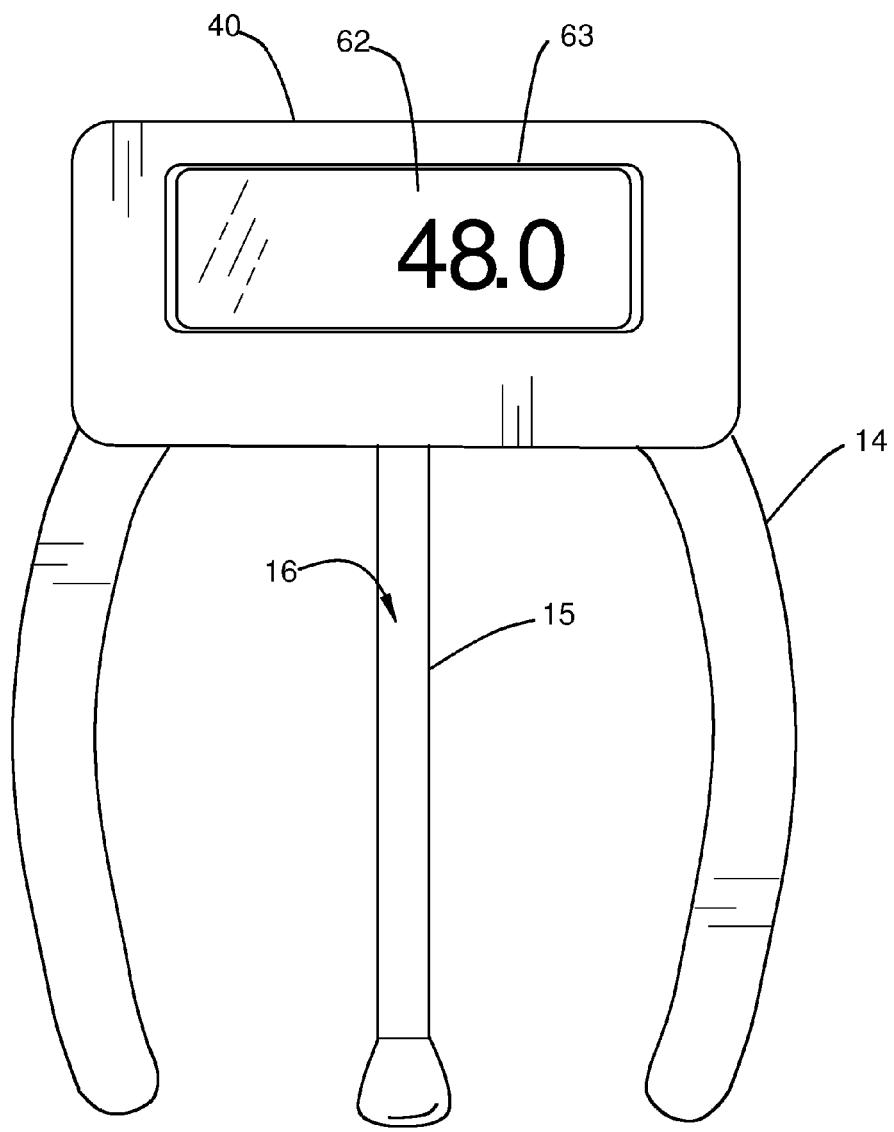
FIG. 1 is top view of one configuration of the invention.
Figure 2:
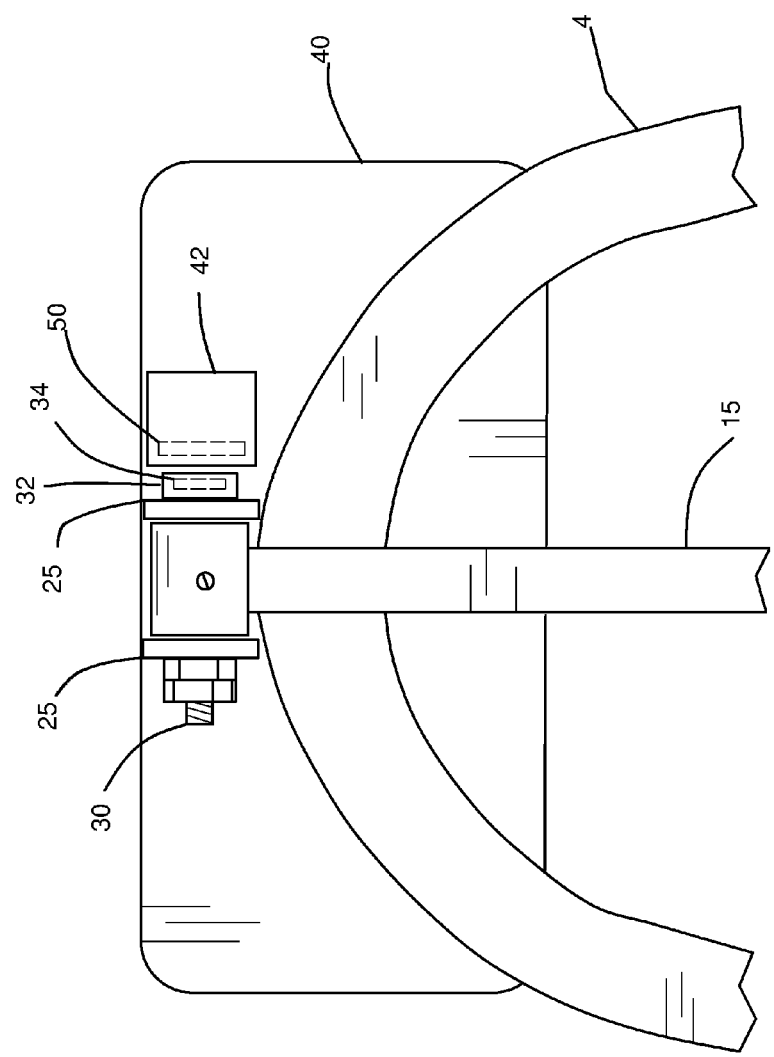
FIG. 2 is partial bottom view of the configuration of FIG. 1 where a portion of the structure has been cut away to allow an enlarged scale.

FIGS. 1 to 5 illustrate a common embodiment of the inventive device. The following discussion and reference numbers regard common elements shown in all of the views. A base plate 14 is formed of rigid material, preferable a noncorroding metal such as brass, bronze, aluminum, iron or steel. The base plate 14 has a base surface 24 that is sized and configured to be placed against and mate to the bottom surface of a horse's hoof. For ease of use and handling, the base plate 14 is shaped, as in the configuration shown, similar to a conventional horse shoe, to match the outer perimeter of the bottom surface a hoof. The general size of the base plate 14 may vary somewhat to accommodate variations in size of horse hoofs. The base surface 24 is preferably flat and planar.

A rigid arm 15 is pivotably connected to the base plate 14 such that in use when the base plate 14 is placed against the bottom of a hoof, the arm 15 can extend against, and be aligned with or on, the forward-most surface of the hoof. The arm 15 must be connected to the base plate 14 at a position to leave the base surface 24 clear and unobstructed to be mated to the bottom of the hoof. The arm 15 may be formed of materials similar to the base plate 14. The overall shape of the arm 15 is not critical, but the arm 15 includes a straight arm aligning surface 16 that faces the base surface 24 to define an acute included angle AB. For ease of use, the arm 15 is preferably elongated with relatively small, but sufficient to be rigid, cross-section.

The manner of pivotably connecting the arm 15 to the base plate 14 may incorporate any of a great variety of mechanisms used for similar purposes. In the configuration shown, the base plate 14 includes two integral pivot flanges 25, each with transverse and aligned through-holes. A proximal end 16 of the arm 15 includes a similar through-hole. In assembly, a pivot rod 30 passes through all the through-holes to provide a structure and means for pivoting the arm 15 between the flanges 25. Threaded fittings are used to secure the pivot rod within the flanges 25. A threaded set screw is located in the arm 15 to bear perpendicularly against the side of the pivot rod 30 and in this way rotationally lock the arm 15 to the pivot rod. The centerline of the flange through-holes should be parallel to the base surface 24 to provide the proper pivoting plane to the arm 15: perpendicular to the base surface 24. It will be clear that alternative constructions and devices may be used to provide a structure or means for providing the arm 15 in a like manner. Optionally, a rotational spring or like biasing means may be incorporated functionally between the arm 15 and base 14 to bias the arm 15 toward the base surface 24 to provide a useful and convenient self-adjusting function.

The pivot rod 30 includes an enlarged head 32 including an open end cavity 33 sized and configured to receive a magnet 34. The enlarged head 32 projects outside the flanges 25 in cantilevered fashion so that the magnet 34 faces outward. The magnet 34 is secured within the cavity 33 with the magnetic poles aligned in a plane perpendicular to the longitudinal axis of the pivot rod 30. The magnet 34 may be secured in any of a variety of ways including using adhesive or another bonding agent. To prevent distortion or masking of the magnetic field of the magnet 34, the enlarged head 32 and pivot rod 30 are preferably formed of brass or other nonferrous metal.

Rigidly secured to the base plate 14 is a rigid enclosure 40. Extending from its top face is an integral sensor enclosure portion 42. Alternatively, the enclosure 40 and sensor enclosure portion 42 may be formed integral to the base plate 14. Likewise, the sensor enclosure portion 42 may be a separate component from enclosure 40, the two then assembled for use.

The sensor enclosure portion 42 is located and aligned to face the pivot rod magnet 34 in close proximity. Within the sensor enclosure portion 42 is securely mounted sensor 50, preferably in form of a Hall Effect device. There are a great variety of similar devices known as Hall Effect devices and among them, for the purposes here, the sensor 50 must be selected or configured to have the capacity to sense relative rotational position of the pivot rod 30 via rotation of the attached magnet 34 and the magnetic field signals thereby received. Other devices known by other names or operating on different principals but providing the same or like function may be equally applied.

To provide satisfactory sensitivity of the sensor 50, depending on the material of the sensor enclosure portion 42, it may be necessary to form the region of the sensor enclosure portion 42 that, after assembly, will be oriented between the sensor 50 and the magnet 34, of relatively magnetically transparent material such as a nonferrous metal or plastic. This requirement may be met by forming the enclosure portion 42 primarily of metal, but with an opening or aperture facing the magnet 34 that is closed and sealed by a sealed covering or hardenable epoxy cement or similar material that provides the needed magnetic properties. These details are not illustrated in the figures for clarity.

An effective sensor device is the integrated circuit device available commercially under the designation MLX90316. This sensor device is a CMOS Hall sensor that gives the angular position of a magnetic field parallel to the IC surface. It is designed for contactless rotary position sensors that are frequently required in both automotive and industrial applications. The device generally detects the absolute angular position of a small magnet (diametrically magnetized) that is positioned and rotates in a plane parallel to the device plane. In this application, the magnet is that (34) located in the pivot arm head 32.

Figure 3:
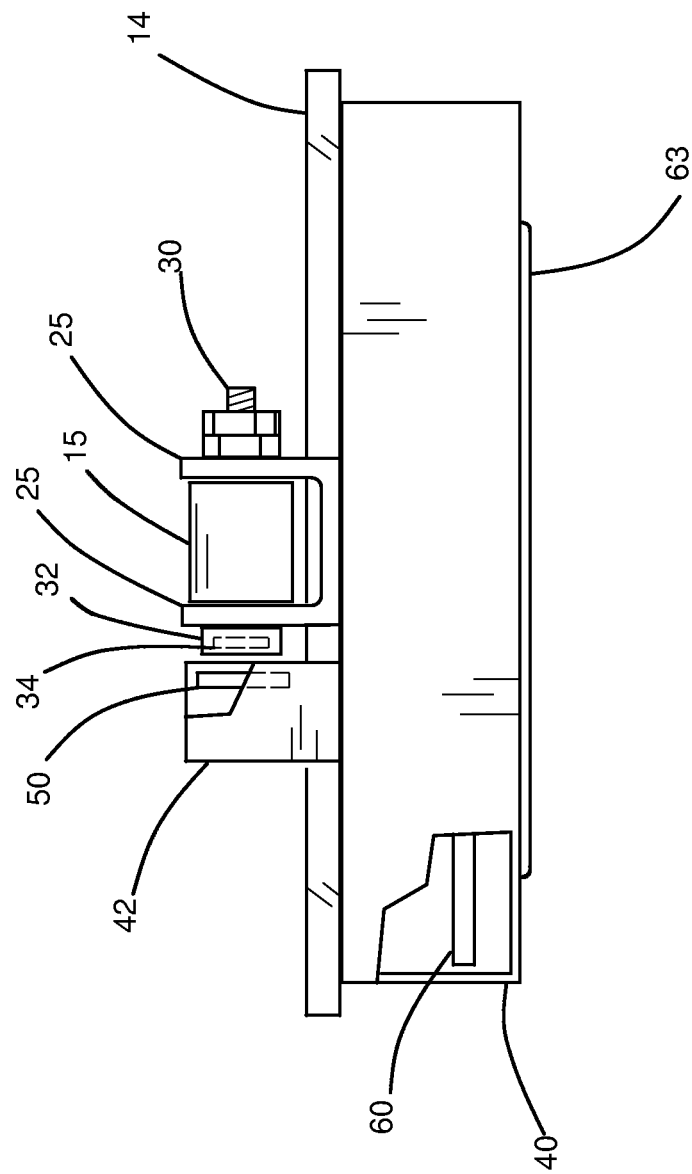
FIG. 3 is back plan view of the configuration of FIG. 1.
Figure 4:
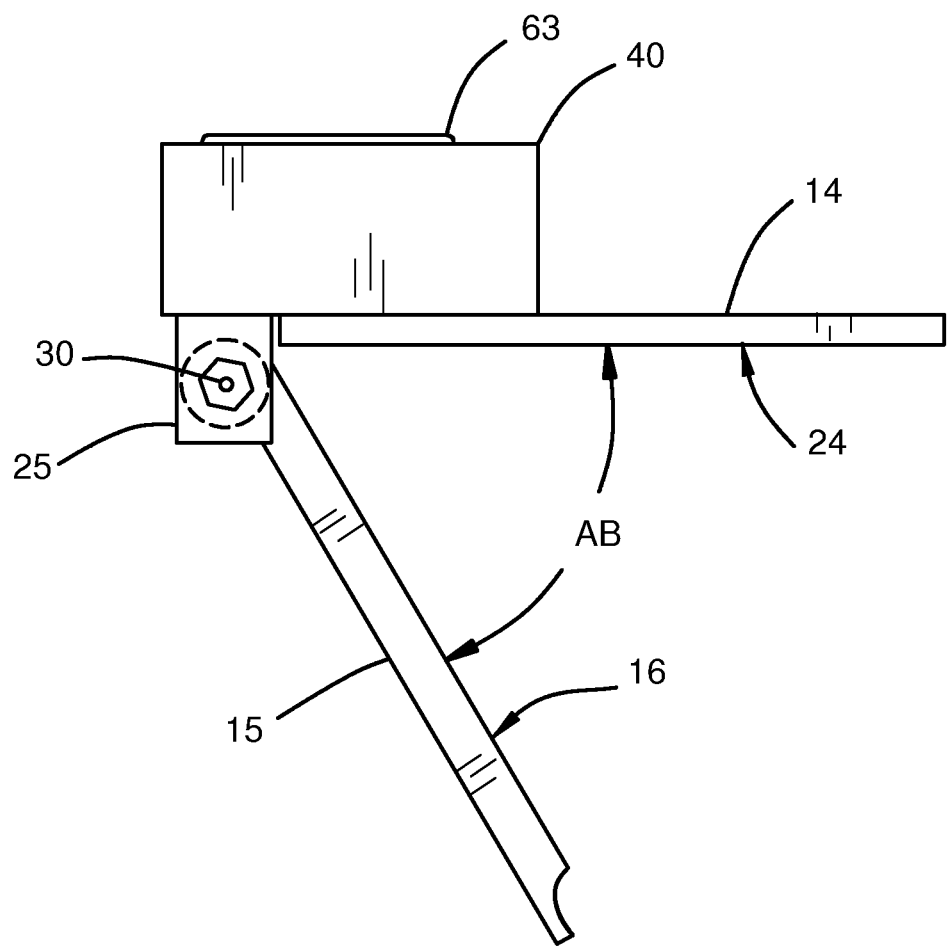
FIG. 4 is a side plan view of the configuration of FIG. 1.

The supporting electronics for the sensor 50 is located in the enclosure 40. Preferably, a printed circuit board (PCB) 60 having the required circuitry (see discussion below) is secured within the enclosure 40 and functionally connected to the sensor 50 via interconnecting circuit wires. The PCB also provides an output display device 62 that is viewable from outside the enclosure 40 through a transparent window 63 in the enclosure 40. In FIG. 1, an exemplary display is shown on the display device 62. The elements in FIG. 3 are partially cut away to view the sensor 50 and the PCB 60. Preferably, the display device 62 includes a screen configured to be visible in bright sunlight or can be back lit for use in darker surroundings.

Figure 5:
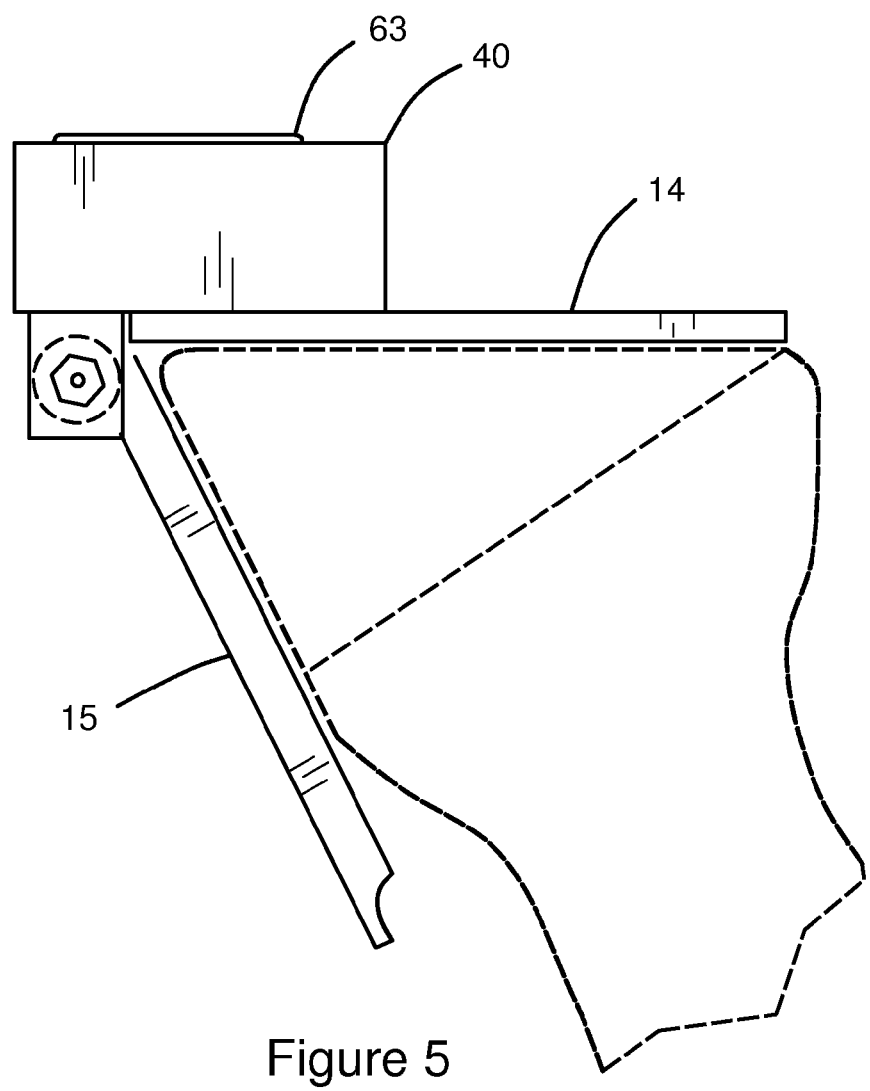
FIG. 5 is a side plan view of the inventive device coupled with a horse hoof in an intended manner of use.

In operation, as shown in FIG. 5, the device is held against the upturned hoof of a horse. The hoof (shown in dashed outline) is stabilized against the base surface 24 such that the base surface 24 is parallel to the plane of interest on the hoof. The hoof is located with the forward edge of the hood against the base of the arm 15 and the aligning surface 16 is then held against the hoof. The sensor 50 receives magnetic field energy as an angle-indicating signal from the magnet 34. The signal is resolved as an absolute angle magnitude by the supporting circuitry which is then displayed. The display device 62, in this orientation facing upward, is easily read by the user in the normal attitude when handling horses.

Figure 6:
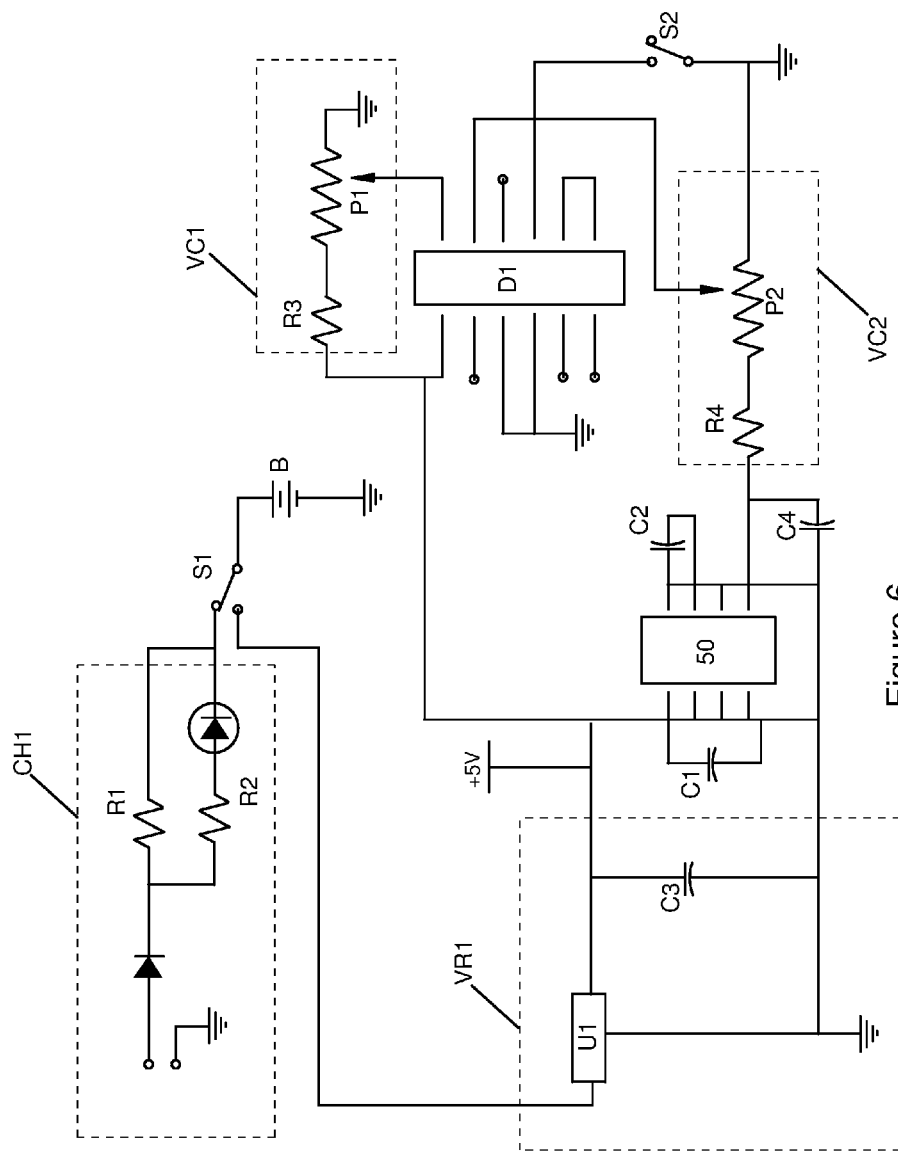
FIG. 6 is a schematic diagram of a sensor circuit according to the invention.

FIG. 6 is a schematic diagram of a sensor circuit that enables the invention. Those elements which are not required to be distinctly mounted within the enclosure 40 are preferably combined onto the PCB. For example the display device component D1 is preferably PCB mounted to enable proper location and orientation. The circuit provides charging elements shown combined as CH1. While access to external power for battery charging is not essential for the invention, such is included for convenience. A battery B provides normal operating voltage and power. A voltage regulating circuit VR1, including a regulator device U1, is connected between the battery B and the sensor device 50. Both calibration circuit elements VC2 and voltage offset control VC1 are included to accommodate variations in particular system components and other factors. The particular component characteristics, and the selection of the appropriate components, for any installation will be discernable to one skilled in design and construction of similar devices. While not illustrated in the figures for clarity, elements such as the charging elements and switch may require control elements such as knobs or physical connections mounted on, or extending through, the external surface of the enclosure 40.

When properly configured and adjusted, the display will provide a digital angle reading corresponding to the angle AB. The relative rotation arm 15 is detected by the associated rotation of the rigidly secured magnet 34. This is accomplished without direct physical connection or contact between the arm 15 and the sensor 50. Because the sensor 50 and its accompanying controls and circuitry are isolated from the arm 15 and the remaining physical components required for hoof angle measurement, the sensor is protected from harm and its operation is ensured. Because the system and sensor 50 are adjustable regardless of the state of the physical components, changes to the arm 15 or other physical components may be accommodated while maintaining overall accuracy.

It is believed that the combination of a Hall Effect sensor and a magnet secured to the rotating arm is an optimum means of measuring relative angle in the hoof angle device. However, other devices operating on different principals may be available now or in the future to similarly providing an angle signaling means that requires no physical contact between the two compared portions of the arm 15 and base surface 24.

The preceding discussion is provided for example only. Other variations of the claimed inventive concepts will be obvious to those skilled in the art. Adaptation or incorporation of known alternative devices and materials, present and future is also contemplated. The intended scope of the invention is defined by the following claims.

The invention claimed is:

1. A hoof measuring device, comprising:
    a rigid base;
    a rigid arm pivotably secured to the base thereby defining an intervening angle;
    a sensor enclosed and rigidly secured to the base, the sensor configured and enabled to detect and determine the intervening angle;
    an electronic circuit connected to the sensor and including a digital display device and configured to display the intervening angle;
    wherein, the base and arm are configured to allow the base to be located against the bottom of a horse hoof while the arm is located against a forward surface of the hoof to define the intervening angle.

2. A hoof measuring device, according to claim 1, and wherein:
    the arm includes a magnet in close proximity to the sensor; and
    the sensor comprises a Hall Effect device.

3. A hoof measuring device, comprising:

a rigid base;

a rigid arm pivotably secured to the base to define an intervening angle;

a sensing means for determining the intervening;

the sensing means secured in a closed enclosure, the enclosure secured to the base; and an electronic circuit connected to the sensing means and including a digital display device configured to display a numeric representation of the intervening angle;

wherein, the base and arm are configured to allow the base to be located against the bottom of a horse hoof while the arm is located against a forward surface of the hoof to define the intervening angle.

4. A hoof measuring device, according to claim 3, and wherein:

the sensing means comprises a Hall Effect device.

* * * * *